United States Patent
Lundeberg et al.

(10) Patent No.: US 9,585,854 B2
(45) Date of Patent: Mar. 7, 2017

(54) N-ACETYL-L-CYSTEINE FOR USE IN IN VITRO FERTILIZATION

(71) Applicant: IASOMAI AB, Lidingo (SE)

(72) Inventors: Thomas Lundeberg, Lidingo (SE); Tiziana Parasassi, Rome (IT); Eugenia Pittaluga, Rome (IT); Roberto Brunelli, Rome (IT)

(73) Assignee: IASOMAI AB, Lidingö (SE)

( * ) Notice: Subject to any disclaimer, the term of this patent is extended or adjusted under 35 U.S.C. 154(b) by 0 days.

(21) Appl. No.: 14/441,104

(22) PCT Filed: Nov. 6, 2013

(86) PCT No.: PCT/EP2013/073182
§ 371 (c)(1),
(2) Date: May 6, 2015

(87) PCT Pub. No.: WO2014/072350
PCT Pub. Date: May 15, 2014

(65) Prior Publication Data
US 2015/0283103 A1    Oct. 8, 2015

Related U.S. Application Data

(60) Provisional application No. 61/724,573, filed on Nov. 9, 2012.

(30) Foreign Application Priority Data

Nov. 9, 2012    (SE) ........................................ 1251274

(51) Int. Cl.
*A61K 31/198* (2006.01)
*A61K 31/4045* (2006.01)

(52) U.S. Cl.
CPC ........ *A61K 31/198* (2013.01); *A61K 31/4045* (2013.01)

(58) Field of Classification Search
CPC .......................... A61K 31/198; A61K 31/4045
USPC ...................................................... 514/562
See application file for complete search history.

(56) References Cited

FOREIGN PATENT DOCUMENTS

| EP | 2305238 | 12/2011 | | |
|---|---|---|---|---|
| WO | WO 2006/116034 | 11/2006 | | |
| WO | WO 2006116034 A1 * | 11/2006 | ........... | C12N 5/0604 |
| WO | WO 2007/003007 | 1/2007 | | |
| WO | WO 2012/130609 | 10/2012 | | |
| WO | WO 2012/130646 | 10/2012 | | |

OTHER PUBLICATIONS

Sanchez-Gutierrez et al. Cell Biology and Toxicology (2008), 24(4), p. 321-329.*
Casao et al. Journal of Pineal Research (2010), 48(1), p. 39-46.*
Fanchin et al., Uterine contractions at the time of embryo transfer alter pregnancy rates after in-vitro fertilization, Apr. 1998, Human Reproduction, vol. 13, No. 7, pp. 1968-1974.
Kim et al., P-463 N-acetyl-cysteine treatment improves insulin sensitivity, ovarian response to gonadotropin and IVF outcome in patients with polycystic ovary syndrome, Jun. 18-21, 2006, Abstracts of the 22nd Annual Meeting of the ESHRE, Prague, Czech Republic, p. i178.
Abstracts of the 22nd Annual Meeting of the ESHRE, Prague, Czech Republic, Jun. 18-21, 2006, downloaded from Human Reproduction at http://humrep.oxfordjournals.org/, pp. i177-i181 (5 total).
Almog et al. "Promoting implantation by local injury to the endometrium" Fertility and Sterility, vol. 94, No. 6, Nov. 2010 (published online Feb. 19, 2010), pp. 2026-2028 (4 total).
Atkuri et al. "N-Acetylcysteine—a safe antidote for cysteine/glutathione deficiency" Current Opinion in Pharmacology, vol. 7, No. 4, Jun. 29, 2007, pp. 355-359 (5 total).
Cavagna et al. "Biomarkers of Endometrial Receptivity—A Review" Placenta, vol. 24, Jul. 8, 2003, pp. S39-S47 (9 total).
Dorn et al. "Serum oxytocin concentration during embryo transfer procedure" European Journal of Obstetrics & Gynecology and Reproductive Biology, vol. 87, Mar. 18, 1999, pp. 77-80 (4 total).
Fanchin et al. "Effects of vaginal progesterone administration on uterine contractility at the time of embryo transfer" Fertility and Sterility, vol. 75, No. 6, Jun. 2001, pp. 1136-1140 (5 total).
Farrell, Susan E. "Intravenous N-Acetylcysteine" Medscape, http://emedicine.medscape.com/article/820200-treatment#d11, Dec. 28, 2008, 6 pgs.
Gustafsson et al. "Global gene expression analysis in time series following N-acetyl L-cysteine induced epithelial differentiation of human normal and cancer cells in vitro" BMC Cancer, 5:75, Jul. 7, 2005, pp. 1-19.
Kalra et al. "In vitro fertilization and adverse childhood outcomes: what we know, where we are going, and how we will get there. A glimpse into what lies behind and beckons ahead" Fertility and Sterility, vol. 95, No. 6, May 2011 (published online Mar. 16, 2011), pp. 1887-1889 (3 total).
Kaneko et al. "Extracellular Matrix Proteins Secreted From both the Endometrium and the Embryo are Required for Attachment: A Study using a Co-Culture Model of Rat Blastocysts and Ishikawa Cells" Journal of Morphology, vol. 274, No. 1, Aug. 9, 2012, pp. 1-10.
Krasnowska et al. "N-acetyl-l-cysteine fosters inactivation and transfer to endolysosomes of c-Src" Free Radical Biology & Medicine, vol. 45, No. 11, Sep. 23, 2008, pp. 1566-1572 (7 total).
Lesny et al. "Embryo transfer—can we learn anything new from the observation of junctional zone contractions?" Human Reproduction, vol. 13, No. 6, 1998, pp. 1540-1546 (7 total).
Mansour et al. "Dummy embryo transfer using methylene blue dye" Human Reproduction, vol. 9, No. 7, 1994, pp. 1257-1259 (3 total).

(Continued)

*Primary Examiner* — Yong Chu
(74) *Attorney, Agent, or Firm* — Haynes and Boone, LLP

(57) ABSTRACT

The invention relates to a new use of NAC in IVF, in a human or mammalian animal patient. In addition an effective dose regimen of NAC in IVF is proposed.

15 Claims, 1 Drawing Sheet

(56) References Cited

OTHER PUBLICATIONS

Moon et al. "Treatment with piroxicam before embryo transfer increases the pregnancy rate after in vitro fertilization and embryo transfer" Fertilility and Sterility, vol. 82, No. 4, Oct. 2004, pp. 816-820 (5 total).

Moraloglu et al. "Treatment with oxytocin antagonists before embryo transfer may increase implantation rates after IVF" Reproductive BioMedicine Online, vol. 2, No. 3, Sep. 2010, pp. 338-343 (6 total).

Nyboe Andersen et al. "Assisted reproductive technology and intrauterine inseminations in Europe, 2005: results generated from European registers by ESHRE" Human Reproduction, vol. 24, No. 6, Feb. 18, 2009, pp. 1267-1287 (21 total).

Nyboe Andersen et al. "Assisted reproductive technology in Europe, 2001. Results generated from European registers by ESHRE" Human Reproduction, http://humrep.oxfordjournals.org/, vol. 20, No. 5, Jan. 21, 2005, pp. 1158-1176 (19 total).

Parasassi et al. "Differentiation of normal and cancer cells induced by sulfhydryl reduction: biochemical and molecular mechanisms" Cell Death and Differentiation, vol. 12, No. 10, May 27, 2005, pp. 1285-1296 (12 total).

Pendyala et al. "Pharmacokinetic and Pharmacodynamic Studies of N-Acetylcysteine, a Potential Chemopreventive Agent during a Phase I Trial" Cancer Epidemiology, Biomarkers & Prevention, vol. 4, No. 3, Apr./May 1995, pp. 245-251 (7 total).

Pierzynski et al. "Oxytocin antagonists may improve infertility treatment" Fertility and Sterility, vol. 88, No. 1, Jul. 2007, pp. 213.e19-213.e22 (4 total).

Pinheiro et al. "Administration of B2-Adrenergic Agonists During the Peri-Implantation Period Does Not Improve Implantation or Pregnancy Rates in Intracytoplasmic Sperm Injection (ICSI) Cycles" Journal of Assisted Reproduction and Genetics, vol. 20, No. 12, Dec. 2003, pp. 513-516 (4 total).

Pittaluga et al. "More than an antioxidant: N-acetyl-L-cysteine in a murine model of endometriosis" Fertility and Sterility, vol. 94, No. 7, Dec. 2010 (published online Jul. 23, 2010), pp. 2905-2908 (4 total).

Poindexter et al. "Residual embryos in failed embryo transfer" Fertility and Sterility, vol. 46, No. 2, Aug. 1986, pp. 262-267 (6 total).

Stolwijk et al. "Cumulative probability of achieving an ongoing pregnancy after in-vitro fertilization and intracytoplasmic sperm injection according to a woman's age, subfertility diagnosis and primary or secondary subfertility" Human Reproduction, vol. 15, No. 1, 2000, pp. 203-209 (7 total).

\* cited by examiner

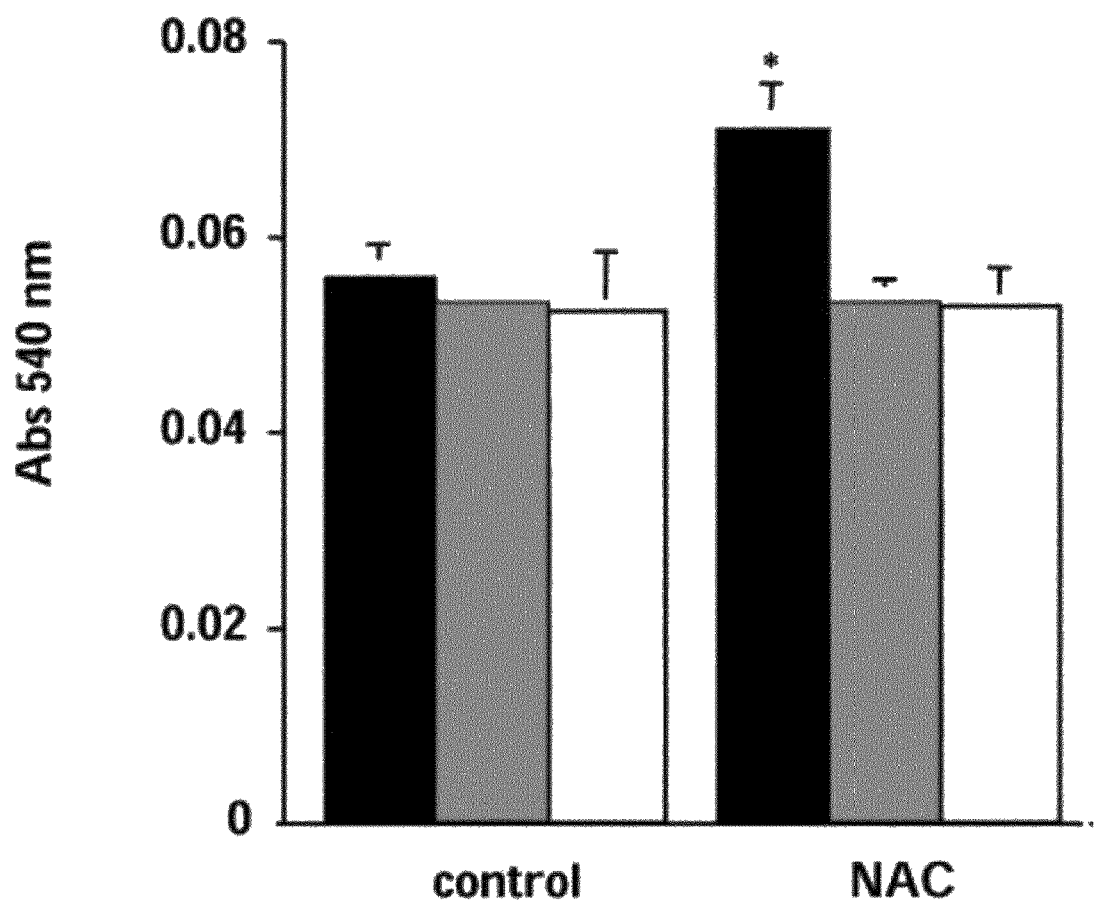

N-ACETYL-L-CYSTEINE FOR USE IN IN VITRO FERTILIZATION

FIELD OF THE INVENTION

The present invention relates to the new use of N-acetyl-L-cysteine in in vitro fertilization

BACKGROUND

In vitro fertilization (IVF) is a process by which an egg is fertilized by sperm outside the body. In vitro IVF is a major treatment for infertility when other methods of assisted reproductive technology have failed. The process involves monitoring a woman's ovulatory process, removing egg or eggs from the woman's ovaries and letting sperm fertilize them in a fluid medium in a laboratory. When a woman's natural cycle is monitored to collect a naturally selected ovum (egg) for fertilization, it is known as natural cycle IVF. The fertilized egg (zygote) is then transferred to the patient's uterus with the intention of establishing a successful pregnancy. The first successful birth of a "test tube baby", Louise Brown, occurred in 1978. Louise Brown was born as a result of natural cycle IVF. Robert G. Edwards, the physiologist who developed the treatment, was awarded the Nobel Prize in Physiology or Medicine in 2010. (S K Kalra et al. Fertility and Sterility Vol 95, no 6 p 1888-1889. In vitro fertilization and adverse Childhood outcomes: what we know, where we are going, and how we will get there. A glimpse into what lies behind and beckons ahead. B Almog et al. Fertility and Sterility Vol 94, No 6 p 2026-2028. Promoting implantation by local injury to the endometrium).

In spite of dramatic progress in assisted reproduction technology over the past 25 years, the overall effectiveness of even the most advanced treatments such as IVF/embryo transfer (IVF/ET) is relatively low, averaging at about 20-30% live births per treatment cycle (Nyboe-Andersen et al., Hum Reprod. 2009; 24(6):1267-87).

Embryo transfer is an independent factor affecting the outcome of the treatment The determinants of success of embryo transfer involve the quality of embryo(s), uterine receptivity and the quality of the intrauterine environment (Cavagna and Mantese, Placenta. 2003; 24 Suppl B:S39-47).

Uterine contractions constitute the most fundamental components of uterine receptivity. Contractile activity of the uterus plays an important role in embryo implantation. Excessive uterine contractions may decrease implantation rates in IVF cycles as contractile activity might expel embryos from the uterus (Fanchin et al. Hum Reprod, 1998; 13: 1968-74). Up to date, treatment strategies to reduce uterine contractions before embryo transfer such as the use of beta agonists or non-steroid anti-inflammatory drugs have not been shown to provide sufficient benefit; Moon et al., Fertil Steril 2004; 82:816-20; Tsirigotis et al. Human Reproduction and Embryology, Jun. 25-28, 2000; Bologna, Italy:).

Treatment cycles induce an abundant increase in oestradiol concentrations which are about 10-20 nmol/l at the end of ovarian stimulation as compared with less than 2 nmol/l before the ovulation in the natural cycle Supraphysiological concentrations of oestradiol are expected to induce local (endometrial) production of oxytocin, formation of oxytocin receptors, and—indirectly—formation/release of PGF2a which is in fact similar to the prelabour status. Also, both oxytocin and vasopressin are involved in induction and maintenance of uterine contractions during labour It has been shown that uterine contractile activity in IVF cycles is increased by approximately 6-fold when measured before embryo transfer as compared with the situation before ovulation in the natural cycle. Uterine contractions play an important role in human reproduction, being actively involved in rapid and directed sperm transport and high fundal embryo implantation In IVF/ET treatments, a progressive decrease in uterine contractions is observed after the egg collection, reaching nearly a quiescent status at the time of blastocyst transfer (5-6 days after egg collection) (Fanchin et al., Fertil Steril 2001; 75: 1136-40). Such a decrease in contractile activity is thought to further augment the higher implantation rates achieved with blastocyst transfers. However, the majority of embryos are still transferred on day 2 or 3 after fertilization, during periods of noticeable uterine contractile activity.

The embryo transfer procedure itself is expected to increase the local oxytocin and prostaglandins release Any additional manipulation of the vagina or cervix, such as the use of a tenaculum, provides an additional stimulus for oxytocin/prostaglandin release (Dorn et al., 1999), which is coupled with increases in uterine contractions). Mansour et al. demonstrated that, in more than half of patients having mock embryo transfer with methylene blue dye, the dye was seen to be transported into the vagina after the procedure (Mansour et al., Hum Reprod 1994; 9: 1257-9). It was also demonstrated that less than 50% of transferred embryos remained in the uterus 1 h after transfer and about 15% of embryos could be found in the vagina after embryo transfer (Poindexteret al. Fertil Steril, 1986; 46:262-7).

Considering the above, it has been suggested that uterine contractile activity at the time of embryo transfer and especially fundo-cervical contractions could expel embryos from the uterus Fanchin et al. Human Reprod 1998; 13:1968-74 have estimated that about 30% of patients undergoing embryo transfer have pronounced uterine contractions. In that group, success rates of IVF/ET treatment were up to 3-fold less compared with the population of patients with 'silent' uteri (16% versus 53% of clinical pregnancies). The difference was independent of the direction of uterine contractions noted during the assessments. That could imply that pharmacological inhibition of increased contractions at the time of embryo transfer could be an attractive target for potential treatment.

Interfering with the PGF2a/oxytocin systems and possibly improving endometrial perfusion could be one mechanism by which uterine contractions would decrease and improve uterine receptivity.

The effectiveness of in vitro fertilization-embryo transfer (IVF-ET) usually does not exceed 30% per treatment cycle (NyboeAndersen A, Gianaroli L, Felberbaum R, de Mouzon J, Nygren K. Assisted reproductive technology in Europe, 2001. Results generated from European registers by ESHRE. Hum Reprod 2005; 20:1158-76) and is further reduced in women older than 36 years. (Stolwijk A, Wetzels A, Braat D. Cumulative probability of achieving an ongoing pregnancy after in-vitro fertilization and intracytoplasmic sperm injection according to a woman's age, subfertility diagnosis and primary or secondary subfertility. Hum Reprod 2000; 15:203-9)

Good quality of embryos and optimal intrauterine environment are the basic determinants of success for ET, and the whole IVF-ET procedure. Ideal intrauterine conditions that enable implantation include appropriate endometrial status, sufficient endometrial perfusion and absence of excessive uterine contractions. In particular, increased uterine contractile activity may expel embryos from the uterus. (Mansour R, Aboulghar M A, Serour G I, Amin Y M. Dummy embryo transfer using methylene blue dye. Hum Reprod 1994; 9:1257-9) (Poindexter A, Thompson D, Gibbons W. Residual embryos in failed embryo transfer. Fertil Steril 1986; 46:262-7)

Implantation and pregnancy rates are inversely correlated with the frequency of uterine contractions and prostaglandin synthesis (PG synthesis). High uterine contractile activity at ET (five or more contractions per minute) is found in about one-third of patients, and in these women clinical pregnancy rates reach 13% per cycle, in contrast to the 53% of successful pregnancies in women with lower uterine activity (three or less contractions per minute) (Fanchin R, Righini C, Olivennes F, Taylor S, de Ziegler D, Frydman R. Uterine contractions at the time of embryo transfer alter pregnancy rates after in-vitro fertilization. Hum Reprod 1998; 13:1968-74.) Moreover, irritation of the uterine cervix by the ET catheter is likely to induce additional PG synthesis and contractile reflexes and further decrease the chances of successful embryo Implantation (Lesny P, Killick S, Tetlow R, Robinson J, Maguiness S. Embryo transfer—can we learn anything new from the observation of junctional zone contractions? Hum Reprod 1998; 13:1540-6.)

However, uterine contractile activity, an important component of uterine receptivity, is currently not a subject of specific diagnosis or treatment in ET recipients. Progesterone supplementation, even when acting on uterine receptivity, improving endometrial status, and decreasing uterine contractions, shows no benefit for pregnancy rates after IVF-ET. (Fanchin R, Righini C, de Ziegler D, Olivennes F, Ledee N, Frydman R. Effects of vaginal progesterone administration on uterine contractility at the time of embryo transfer. Fertil Steril 2001; 75:1136-40.)

Studies assessing the effectiveness of piroxicam (cyclooxygenase inhibitor) and ritodrine (β2-adrenoreceptor agonist) have shown a positive effect on pregnancy rates. (Moon H, Park S, Lee J, Kim K, Joo B. Treatment with piroxicam before embryo transfer increases the pregnancy rate after in vitro fertilization and embryo transfer. Fertil Steril 2004; 82:816-20; Tsirigotis M, Pelekanos M, Gilhespie S, Gregorakis S, Pistofidis G. Ritodrine use during the peri-implantation period reduces uterine contractility and improves implantation and pregnancy rates post-implantation. Presented at the 16th annual meeting of the European Society of Human Reproduction and Embryology; Jun. 25-28, 2000; Bologna, Italy). The drugs mentioned above have failed to enter routine clinical use because of safety concerns.

Recently, Moraloglu et al. Treatment with oxytocin antagonists before embryo transfer may increase implantation rates after IVF. Reproductive biomedicine online Sep. 2010; 21(3): 338-43 reported a randomized, placebo controlled trial with a total i.v. dose of 37.5 mg of atosiban (oxytocin antagonist) infused before and up to 2 h after the embryo transfer in 160 patients. The authors noted significant improvement in both implantation rates and clinical pregnancies. Implantation rates per embryo transferred were 20.4% versus 12.6% and clinical pregnancy rates per cycle were 46.7% versus 28.9% (atosiban versus placebo). Fewer early miscarriages were noted in the study group (16.7% versus 24.4%, atosiban versus placebo).

N-acetyl-L-cysteine (hereinafter referred to as NAC) is a well-known drug, which has been used mainly as a mucolytic agent and in the treatment of paracetamol poisoning. In recent years it has also been acknowledged as having other beneficial properties, such as being anti-inflammatory and anti-proliferative, and has been suggested for the treatment of a variety of different disorders and symptoms in addition to endometriosis also schizophrenia, diabetes and cancer.

To date, NAC has not been considered a drug in fertility treatment although it has been used for oral treatment of endometrioses as described in EP 2305238. In that study no conclusions about pregnancies were made. To the contrary when being treated for endometriosis it was not expected that any pregnancies could occur. Although, it has not been disclosed before, when analysing the data the inventors have noticed that there was one person who had taken NAC orally for endometriosis had a successful IVF treatment. Also two previous IVF trials had failed and resulted in an abortion. This was one of the reasons why the present inventors started investigating whether NAC could be used in connection with IVF.

Indeed, in mice, NAC was confirmed to support embryo implantation. In the animal model, embryo implantation rate was decreased when the mice were given oxytocin. NAC dose-dependently restored implantation rates in oxytocin-treated mice, which provided evidence for involvement of oxytocin in embryo implantation.

PRIOR ART

Background art, describing the molecular effect of NAC in the treatment of cancer, include: T. Parasassi, et al. Cell Death and Differentiation (2005), Vol. 12, No. 10, pages 1285-1296; E. K. Krasnowska et al. Free Radicals Biology and Medicine 2008, 45(11):1566-72; A. C. Gustafsson et al. BMC Cancer (2005), 5:75. NAC in the treatment of endometriosis is described in Pittaluga et al. More than an antioxidant: N-acetyl-L-Cysteine in a murine model of endometriosis. Feral & Steril 2010; 94(7): 2905-8. Further, C. H. Kim et al. (Abstracts of the 22nd Annual Meeting of the ESHRE, Prague, Czech Republic, 18-21 Jun. 2006, P-463) describe treatment with N-Acetyl-Cysteine to improve insulin sensitivity. Formulations containing N-acetyl-L-cysteine(NAC) as such or together with (ii) selenium in the form of selenomethionine and/or (iii) melatonin and/or physiologically acceptable salts thereof are described in EP 12710062.6. Such formulations may also be used for treatment of IVF.

OBJECTS OF THE INVENTION

Already from the start of IVF it has been a problem that the clinical outcome in IVF treatment is low. As the cost of IVF is high and the treatment normally only give 20-30% live births per treatment cycle, many different treatments have been tested in order to give a higher percentage of live births. It has now unexpectedly been found that administration of NAC preferably a few days prior to IVF treatment gives a higher percentage of live births. Further, in cases where many earlier IVF treatments have been unsuccessful, the prior administration of NAC in connection with a new IVF treatment have resulted in live births.

The clinical outcome of NAC treatment as defined in the claims of the present application in in vitro fertilization (IVF) has, to the knowledge of the inventors, not been determined in the prior art, nor has an efficient dosage regimen for the treatment of IVF or the use of NAC for the treatment of indications associated with IVF been proposed.

It is therefore a general object of the present invention to provide a solution to the problem of providing a pharmaceutical composition comprising N-acetyl-L-cysteine (NAC) for the treatment of IVF and indications associated with IVF in humans and mammals.

SUMMARY OF THE INVENTION

According to the present invention a pharmaceutical composition comprising N-acetyl-L-cysteine (NAC) is used for intravenous and/or oral administration. The formulation contains N-acetyl-L-cysteine (NAC) as such or together with (ii) selenium in the form of selenomethionine and/or (iii) melatonin and/or physiologically acceptable salts thereof.

The formulation with NAC as such contains between 70-150 mg/kg body weight of NAC and is administered once a day for 1-3 days in connection with IVF treatment. It is also possible to administer only once, namely on the day of IVF administration. In that case the administration takes place about 1 hour before IVF.

EXAMPLES

Embryotoxicity

The eventual occurrence of NAC embryotoxicity was preliminary tested. To verify the embryotoxicity of NAC the application of two embryotoxicity tests—rabbit embryo bioassay and human sperm motility bioassay—were used (see Pierzynski et al., 2007a). Both failed to detect an embryotoxic effect of NAC in concentrations up to 50-fold therapeutic blood concentrations. NAC was shown not to affect the survival of 1-cell rabbit embryos, as well as not to decrease the percentage of hatched rabbit blastocysts. Tests performed on human spermatozoa also failed to show an adverse influence.

Toxicity Test—Human Sperm Motility Bioassay

Assessments of human sperm motility were performed on fresh samples taken from 3 healthy donors with good seminal parameters including sperm motility and velocity. Migration or "Swim-up" on human sperm preparation medium was applied to select motile spermatozoa. After selection each semen sample was divided into 3 aliquots transferred to Eppendorf tubes. In addition to one control tube, two tubes had NAC added at concentrations of 100 and 1,000 nM. Tubes were incubated in a 5% $CO_2$ environment, with constant temperature and humidity conditions for 24 hours. Sperm motility was assessed using a contrast phase microscope at a 400 times magnification after 1, and 24 hours of exposure to NAC. Assessment was performed over a fixed time interval of 2 minutes. Nine samples were assessed for sperm motility and velocity by 36 measurements (2 measurements at 1 and 24 h per sample).

In the human sperm motility bioassay assessments, no effects of NAC on human sperm motility or velocity were detected when compared to controls. However, the duration of the experiment influenced motility, detected as a gradual decrease of activity and velocity of spermatozoa. This decrease was seen in both controls and NAC treated and did not differ between the groups. No interactions between time and concentration were found, so the effect of time did not differ significantly in the 2 groups of concentrations 100 and 1,000.

In Vitro

Integrins are expressed in a highly regulated manner at the maternal-fetal interface during implantation. However, the significance of extracellular matrix (ECM) ligands during the integrin-mediated embryo attachment to the endometrium is not fully understood. Thus, the distribution of fibronectin in the rat uterus and blastocyst was studied at the time of implantation. Fibronectin was absent in the uterine luminal epithelial cells but was intensely expressed in the trophoblast cells and the inner cell mass suggesting that fibronectin secreted from the blastocyst may be a possible bridging ligand for the integrins expressed at the maternal-fetal interface. An Arg-Gly-Asp (RGD) peptide was used to block the RGD recognition sites on integrins, and the effect on rat blastocyst attachment to Ishikawa cells was examined. There was a significant reduction in blastocyst attachment when either the blastocysts or the Ishikawa cells were pre-incubated with the RGD-blocking peptide. Thus, successful attachment of the embryo to the endometrium requires the interaction of integrins on both the endometrium and the blastocyst with the RGD sequence of ECM ligands, such as fibronectin. Pre-treatment of both blastocysts and Ishikawa cells with the RGD peptide also inhibited blastocyst attachment, but not completely, suggesting that ECM bridging ligands that do not contain the RGD sequence are also involved in embryo attachment (Kaneko Y, Murphy C R, Day M L. Extracellular matrix proteins secreted from both the endometrium and the embryo are required for attachment: A study using a co-culture model of rat blastocysts and Ishikawa cells. J Morphol. 2013; 274(1):63-72)

Experiment 1

The present experiments were carried out to elucidate if NAC treatment influence junction (adhesion) proteins including integrin/fibronectin.

Cell Adhesion Assay. Seven μg/ml of human fibronectin (Sigma Aldrich Chem Co) were saturated with 2% bovine serum albumin (BSA) for 30 min at 37° C. and washed twice with phosphate buffered saline (PBS). Jurkat cells were then seeded onto the wells for 2 h at 37° C.; then, nonadherent cells were aspirated, and the wells were rinsed with PBS. Adhering cells were fixed overnight with 2% formaldehyde and stained with eosin Y for 30 min. Eosin Y was then extracted by addition of a mixture of 1% of glacial acetic acid and 50% ethanol, and absorbance was measured at 540 nm.

Integrin alpha-4 (VLA-4) expression. VLA-4 antigen expression was detected on Jurkat cells by indirect immuno fluorescence with a monoclonal anti-VLA-4 (clone HP1/7) and flow cytometry. Staining of cells was performed according to standard protocols and flow cytometry analysis was performed by using a FACS-Calibur cytometer (Becton Dickinson).

Results With Reference to FIG. 1

NAC increases the adhesions of Jurkat cells on fibronectin. The adhesion assay was performed by using control or NAC (5 mM for 2 h)-treated Jurkat cells. The cells were photographed after staining with eosin Y. Incubation of the cells, after NAC treatment, with anti-VLA-4 antibody, inhibited adhesion. Cell adhesion was then quantitated by staining the cells attached to junction protein-coated plates with eosin Y and reading the absorbance in a microplate reader. As shown in FIG. 1, NAC pretreatment augmented cell adhesion by nearly 35%, an effect that was abolished by anti-VLA-4.

Cells were solubilized and eosin Y and absorbance was quantitated at 540 nm. No antibody, illustrated by black bars; anti-VLA-4 (10 ng/ml) illustrated by grey bars; and anti-VLA-4 (10 μg/ml) illustrated by white bars. Data are means+/−SE($n$=3).*, P less than 0.01 vs. control. From FIG. 1 it can be concluded that NAC treatment increases adhesion (junction protein molecules).

Experiment 2

The present experiments were carried out to elucidate if NAC treatment influence integrin and fibronectin gene expression by gene expression analysis using the Affymetrix GeneChip platform.

A micro array based gene expression analysis of the normal human epidermal keratinocytes was performed 1 and 12 hours after addition of NAC, compared to untreated (i.e. control samples at the same time points). Data obtained from GeneChip analysis were processed using the RNA analysis approach and samples were normalized to their corresponding controls. Filtering was done based on two criteria (p-value <0.1 and >1.5 fold up- or >0.5 down-regulation) for each time point. The labelling and hybridisation was done in duplicate.

1 hr after NAC treatment integrin alpha 2, was found up-regulated. At 12 hours fibronectin was found to be upregulated. These results suggest that NAC treatment results in an increased adhesion through the sequential up-regulation of integrin and fibronectin and that some of the effects are seen already one hour after treatment.

Experiment 3

In mice, NAC was confirmed to support embryo implantation. In the animal model, embryo implantation rate was decreased when the mice were given oxytocin. NAC dose-dependently restored implantation rates in oxytocin-treated mice, which provided evidence for involvement of oxytocin in embryo implantation.

To verify the embryotoxicity of NAC the application of two embryotoxicity techniques—rabbit embryo bioassay and human sperm motility bioassay—were used. Both failed to detect an embryotoxic effect of NAC in concentrations up to 50-fold therapeutic blood concentrations. NAC was shown not to affect the survival of 1-cell rabbit embryos, as well as not to decrease the percentage of hatched rabbit blastocysts. Tests performed on human spermatozoa also failed to show an adverse influence.

Experiment 4

Animal Model Showing that NAC Decreases the Contractions of the Uterus
Experimental Design
Animals were kept at 22° C., housed 3 per cage and fed ad libitum. Isolated uteri from virgin Wistar rats (200-280 g) in estrous, which was determined by examination of a daily vaginal smear, were used.
Reagents
Protamine sulphate (PS) and NAC were dissolved in pure water.
Isolated Organ Bath Studies
All rats were sacrificed by cervical dislocation. The uterine horns were excised, carefully cleaned and mounted vertically in a 10 ml volume organ bath containing De Jalon's solution (NaCl 154 mM, KCl 5.6 mM, $CaCl_2 \times 2H_2O$ 0.41 mM, NaHCO 2 5.9 mM and glucose 2.8 mM), under 1 g tension, aerated with 95% oxygen and 5% carbon dioxide at 37° C. After an equilibration period (of 45 min), when uteri showed stable contractions (spontaneous or calcium ion-induced), indometacin (1 µg/ml) was added prior to PS. After 10 min increasing concentrations of PS were added until the total cessation of contractions was observed.

Myometrial tension was recorded isometrically with an organ bath and transducer.
Data Analysis and Statistical Procedures
Effects of treatments on uterine contractions were calculated as percentages for control, untreated and contracting conditions. Each data value is expressed as the mean±SEM. differences between groups were analyzed by two-way ANOVA. EC50 values were compared using one-way ANOVA
Results
PS caused dose-dependent relaxation of spontaneously active uteri. NAC pre-treatment (1 µg/ml) increased PS-induced relaxation. PS also caused dose-dependent relaxation of calcium ion-induced uterine contractions. NAC pre-treatment modulated PS-induced relaxation of uterine contractions and changed the curves of PS-induced relaxation.

The EC50 values for PS-treated uteri were analyzed. Significant differences in EC50 values were found with regard to the type of contraction used and the treatment used. The EC50 was lower in spontaneously active uteri than in calcium ion-induced uteri. The EC50 values for spontaneously active uteri pretreated with indometacin (1 µg/ml) were significantly lower than the other two EC50 values obtained. However, calcium ion-induced active uteri pretreated with indometacin presented higher EC50 values when compared to PS-treated uteri.

DETAILED DESCRIPTION OF THE INVENTION

NAC in General
N-acetyl-L-cysteine (NAC) is a well known low molecular weight pharmaceutical drug, with the chemical formula

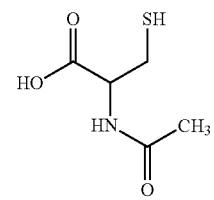

NAC

The features of NAC are mainly related to its thiol group, which makes it effective in most biochemical pathways were the tripeptide glutathione (GSH), present in all human tissues at relatively high concentrations, even above 10 mM, acts. Cysteine is indeed among the three amino acids composing GSH, so NAC is considered a precursor of GSH with its de-acetylated cysteine. NAC has been and still is largely used as a mucolytic agent, where the mode of action is generally attributed to the redox breakage of sensitive cysteine disulfur bridges in the mucus proteins. In fact NAC participates to the complex redox cycling of thiol groups, where several enzymes act. Indeed, of extreme physiological importance is the disulfide formation and breakage cycle, a common mechanism by which protein activity and cellular signaling is regulated. Enzymes such as protein tyrosine phosphatases and tyrosine kinases, for example, play pivotal roles in the control of the cell cycle, cell proliferation and differentiation, and many of them are regulated by the redox state of their cysteines.

Overall, although detailed mechanisms of action have not been finally elucidated, NAC appears to act in all biochemical pathways where GSH does. Enzymes and proteins whose activity is modulated by GSH operate is several processes either directly or through a net of signals transduction pathways. In this picture, NAC may either parallel GSH action, or may be even more effective than GSH.

GSH is e.g. normally conjugated to reactive metabolites formed by paracetamol and helps detoxify them. When paracetamol is overdosed GSH is however depleted and the paracetamol metabolites start reacting with cellular proteins, eventually leading to cell death. In the treatment of fulminant hepatic failure after paracetamol poisoning NAC acts instead of GSH in the detoxification of paracetamol metabolites. NAC is believed to be virtually absent of undesired side effect, which is also indicated by the high NAC doses that are used in the treatment of paracetamol poisoning, estimated, for a 70 kg individual, of about 40 g/day.

Contrary to the tripeptide GSH, which can be degraded already in stomach, the simple NAC molecule freely diffuses in almost all tissues and cells. NAC pharmacokinetic studies determined a peak concentration in plasma reached in about one hour, with a half-life of about three hours. Total clearance occurs between six and twelve hours.

NAC as an Antiproliferative, Differentiating Agent

The inventors have recently found that N-acetyl-L-cysteine (NAC) possesses a marked antiproliferative effect on cancer cells of epithelial origin (Cell Death and Differentiation 2005, 12(10): 1285-1296).

NAC was used to arrest proliferation and induce differentiation in two adenocarcinoma cell lines and in primary normal keratinocyte cells, all of epithelial origin. In these systems, the differentiation was characterized morphologically, biochemically and through gene expression analysis (the gene expression analysis extensively reported in BMC Cancer 2005, 5: 75).

The antiproliferative effect of NAC, in the study of cancer, was not related to cell death or to toxicity but, instead, was due to the activation of a physiological differentiation pathway, which can be regarded as a normalization of cell functions towards the tissue of origin.

In addition to the decreased proliferation, the morphology of NAC-treated cancer cells was also altered. In vitro, epithelial cells under active proliferation display an irregular morphology—a mesenchymal morphology—and often form several multiple cell layers. On the contrary, when cells undergo a differentiation process, toward the structure and function of their final target tissue, they stop proliferation, their morphology becomes regularly polygonal, each cell sometimes thicker, and they form a single layer of adjacent cells. This process is accompanied by increased cell-cell and cell-substratum junctions, consistent with a shift from a proliferating mesenchymal to an adhesive, less motile and differentiated phenotype.

On a whole, a complex series of metabolic changes were detected after NAC supplementation to cancer cells, all converging in arresting the uncontrolled proliferation and in inducing their terminal differentiation. Notably, NAC treatment induced a considerable increase in cell-cell and cell-substratum adhesion complexes. Uncontrolled proliferation can be regarded to as a condition where cells have lost the contact inhibition and their ability to respond to differentiation signals. Cells entering the differentiation pathway exhibit a noticeable increase in cell-cell junction complexes, and the process is also generally indicated as contact inhibition. Several evidences indicate that signals for the cells to enter the differentiation end-point originate from the components of cell-cell complexes themselves. These junctions are also a way for the diffusion of signals between cells.

Dosage Regimen

From the study of NAC treatment on adenocarcinoma cell lines and primary normal keratinocyte cells (Cell Death and Differentiation 2005, 12(10): 1285-1296), it was concluded that the effective dose of NAC for induction of the antiproliferative-differentiating effect varied and was cell type dependent. The tissue of origin thus dictates the effective NAC concentration required to observe a complete block of proliferation, and has to be determined for each tissue. In addition, the dose of NAC was also related to the cell malignancy. In detail, while normal cells required a low dose to stop proliferating and start differentiating, carcinoma cells with characteristic poorer prognosis required a higher NAC concentration.

For the purpose of the present invention a dosage regimen of NAC for the treatment of IVF in a mammal, including human, was developed based on the following criteria:
1) a dosage of NAC per day which is in agreement with other current clinical treatments and is considered without undesirable side effects;
2) given a reported decrease in NAC plasma level after prolonged treatments (Pendyala L, Creaven P J. Cancer Epidemiol Biomarkers Prev. 1995; 4:245-51), the suspension of the treatment for about half of each week was considered for an optimal biological response in a treatment for two months or longer.

The composition of the present invention, comprising NAC for the treatment of IVF according to one embodiment to be administered intravenously at a dose between approximately 50 and 150 mg/kg/day. The lower limit has been shown to be effective in IVF and the higher limit is known to have virtually no side effects.

In still another embodiment of the present invention the composition comprises NAC to be administered orally at a dose of approximately 30-45 mg/kg/day. This low dosage has surprisingly been shown to be effective in the treatment of endometriosis and also give effect in connection with IVF.

In one embodiment the oral composition is to be administered for a period of time which is two months or more, or preferably three months or more. To counteract a decrease in NAC plasma level after prolonged treatment NAC may be administered at the prescribed dosage in an intermittent fashion, i.e. intermittent dosage regimen/treatment. By intermittent administration or treatment is meant that the treatment is interrupted in periods, i.e. that the pharmaceutical composition is administered for a period of time, e.g. a few days, followed by an interruption in administration, where no pharmaceutical composition is administered for a period of time, e.g. for a few days. Intermittent treatment can be regular, e.g. treatment for a fixed number of days or weeks, followed by interruption for a fixed number of days or weeks. Examples include repeated schemes with treatment for 4 days followed by interruption for 3 days each week or treatment for 2 weeks followed by interruption 1 week. A special case of regular intermittent treatment is pulsed treatment, i.e. with regular treatment and interruption duration, e.g. administration every other day or administration for two days followed by two days of interruption etc. Irregular intermittent treatment schemes that are not regularly repeated or have a more complex scheme that is repeated is also conceivable, e.g. dependent on response to treatment. In different exemplifying embodiments of the present invention the prescribed dose of NAC is administered for 3-5 consecutive days followed by 2-4 days of interruption, or administered for 1-3 consecutive days followed by 1-2 days of interruption.

In one embodiment, by referring to a body weight of approximately 60 kg, the NAC dose is in the range between 1.2 and 5.4 g/day, preferably between 1.8 and 3.6 g/day. The dose may be divided in two or more, preferably three or four, daily administrations of either one or two doses (e.g. pills) each, where each dose may comprise e.g. 0.15-2.7 g of NAC or preferably 0.6-1.2 g of NAC. The treatment includes the administration of the above mentioned doses pulsed or intermittently, e.g. every other day or for three to four consecutive days each week, with a suspension from four to three days, respectively. The minimum total duration of the treatment is of two months, with no maximum duration. For patients with other weights, e.g. over- or underweight persons the daily dose needs to be adjusted accordingly.

In one embodiment of the present invention the pharmaceutical composition for treatment of IVF NAC in a dose of 150-5400 mg to be administered in two or more administrations per day, for a period of at least 2 months, such as at least 3 months. In a preferred embodiment of the present invention the pharmaceutical composition comprises NAC in a dose of 230-3600 mg to be administered in two or more administrations per day, for a period of at least 2 months, such as a maximum of at least 3 months. The treatment includes the administration of the above mentioned doses pulsed or intermittently, e.g. every other day or for three to four consecutive days each week, with a suspension from four to three days, respectively.

NAC may also be administered together with selenium in the form of selenomethionine and/r melatonin. Such combinations are further described in EP 12710062.6

Pharmaceutical Formulations

A pharmaceutical composition according to the present invention may be prepared in a manner per se known by a person skilled in the pharmaceutical art. The composition may comprise an effective amount of NAC, in accordance with the invention, as well as a suitable carrier or excipient that serves as a vehicle or medium for the active ingredient. Such carriers or excipients are known in the art. The pharmaceutical composition is preferably for iv administration Other forms, such as tablets, capsules, suppositories, suspensions, syrups or the like are also conceivable. The invention requires a strict assessment of the pharmaceutical quality of NAC preparation for obtaining the effective dose. Therefore, brand or certified generic preparations have to be used. NAC is not a stable molecule, its active thiol residue can be easily oxidized by oxygen, light and other radiations, so that the effective dose would not be reached. The preparation is thus preferably protected from light, in soluble tablets, with sodium hydrogen carbonate, which helps in a partial removal of oxygen from water during dissolution.

It has been observed that high oral doses of NAC may cause abdominal pain. For overcoming this in cases of oral administration, an option is to provide NAC in a formulation with gastric protection, suitable for preventing NAC release/solubility in the stomach. Such formulations are well known in the art and may be used with the present invention. For example, tablet coatings that are resistant to gastric fluids and allow release of the drug only in the intestine, after its transit through the stomach, may be used. Commonly used formulations include polymers such as cellulose derivatives, methacrylate amino ester copolymers. The coating protects the tablet core from disintegration in the acidic environment of the stomach by employing pH sensitive polymer, which swell or solubilise after having passed through the stomach, in response to an increase in pH, to release the drug.

Another option is to lower the dose of NAC entering the blood stream at one time. Administration of NAC three or more times daily can be difficult to accomplish for the patient. Nevertheless, a repeated administration can be desirable to achieve a nearly constant serum concentration of NAC. To overcome these problems, a once or twice-a-day administration could be easier to handle for the patient, for instance morning and night. One option is to provide NAC in a slow-release formulation (also denoted sustained-release or controlled-release). By being able to reduce the rate of diffusion and uptake of NAC into the blood stream, such a formulation enables administration of a larger dose at longer intervals. The dose is then distributed in the blood over a long time in small quantities, e.g. over 12+12 hours in the case of a twice-a-day regimen scheme. Many different technologies and formulations for slow-release are since long known in the art and may be applied with the present invention. In such technologies the active substance is for example encapsulated in a coating or matrix that is insoluble or less soluble in the body fluid where it is administered.

Formulations having a combined effect of slow-release and gastric protection is also possible and may be used within the present invention.

Examples in Human

Administration in Connection with IVF Treatment

The very first case of clinical application of NAC prior to embryo transfer was recently documented. NAC was administered in a concentration of 50 mg/kg to a 42-year-old patient who had previously undergone five embryo transfers involving a total number of 8 good-quality embryos. Immediately before embryo transfer, the presence of increased uterine contractile activity was confirmed by ultrasound. NAC 50 mg/kg body weight was administered in intravenous infusion for 60 min. Embryo transfer was carried out 60 min from the end of the 60 min NAC 50 mg/kg body weight administration. Both before connecting the infusion and directly before embryo transfer, a transvaginal sagittal scan recording was performed. Thereby it was possible to confirm that uterine contractions decreased from 10 contractions per 3 min to five contractions per 3 min as well as recording an apparent decrease in their amplitude. Therapeutic success was confirmed by the delivery of a healthy daughter.

Pulsed Administration

Below is the result from giving pulsed administration of NAC to 15 patients, 8 of which became pregnant.

According to this, NAC was administered to patients per os for 3 months or more according to the following schedule: 600 mg three times a day, three consecutive days a week. The adoption of this procedure was based on the following considerations: (1) the daily total NAC dose of 1.8 mg is virtually free of side effects and was already considered for other clinical indications [K. R. Atkuri, J. J. Mantovani, L. A. Herzenberg, and L. A. Herzenberg, "N-acetylcysteine-a safe antidote for cysteine/glutathione deficiency," Current Opinion in Pharmacology, vol. 7, no. 4, pp. 355-359, 2007.]; (2) splitting the total dose in 3 is simple for patients and, with reference to the known NAC pharmacokinetics [L. Pendyala and P. J. Creaven, "Pharmacokinetic and pharmacodynamic studies of N-acetylcysteine, a potential chemopreventive agent during a phase I trial," Cancer Epidemiology Biomarkers and Prevention, vol. 4, no. 3, pp. 245-251, 1995.], grants a nearly constant plasma level of the drug; (3) the four-day medication-free interval provides a washout period useful to limit the reported decrease of NAC plasma level observed during prolonged treatments.

Results

| Patient | months of attempt of pregnancy | pregnancy after months post NAC treatment | type of pregnancy (1st or 2nd) |
|---------|-------------------------------|-------------------------------------------|-------------------------------|
| 1 | 12 | 1 | 1 |
| 2 | 12 | 1 | 1 |

-continued

| Patient | months of attempt of pregnancy | pregnancy after months post NAC treatment | type of pregnancy (1st or 2nd) |
|---|---|---|---|
| 3 | 60 | 19 | 1 |
| 4 | 1 | 8 | 1 |
| 5 | 6 | 6 | 1 |
| 6 | 48 | 0 | 2 |
| 7 | 1 | 14 | 1 |
| 8 | 12 | 3 | 1 |

Formulations to be Used in Connection with the Invention

In one embodiment the invention provides a pharmaceutical composition comprising N-acetyl-L-cysteine (NAC) for intravenous administration of between 50-150 mg/kg body weight of NAC once a day for 1-3 days in connection with IVF treatment.

One aspect is a pharmaceutical composition comprising NAC for use in a dose of 150 mg/kg for 1-3 days.

Another aspect is a pharmaceutical composition comprising NAC for use only on the same day as IVF treatment.

In still another embodiment of the present invention the composition comprises NAC to be administered orally at a dose of approximately 30-45 mg/kg/day.

When NAC is combined with selenium and/or melatonin NAC is administered at a dose of 5-45 mg/kg/day, selenium, in the form of selenomethionine, for administration at a dose of 0.4-1.2 n/kg/day and melatonin for administration at a dose of 0.02-0.08 mg/kg/day. The medical product is in one embodiment a pharmaceutical composition comprising NAC, selenium in the form of selenomethionine, and melatonin.

Also the pulsed or intermittent, oral administration, for a time period of three months, at a dose of N-acetyl-L-cysteine that is between 20 and 90 mg/kg/day on days when administered will give a beneficial effect on success of IVF. In that case the composition is for continuous administration for three months or more, or 3-5 consecutive days followed by 2-4 days of interruption. In another embodiment the pharmaceutical composition comprising N-acetyl-L-cysteine is for administration for 1-3 consecutive days, followed by 1-2 days of interruption.

According to examples described in the specification 15 patients were treated with pulsed administration of N-acetyl-L-cysteine for use in IVF orally in a dose of 600 mg three times a day during three consecutive days followed by four days of interruption during 3 months or more.

Other possible administration regimens such as the following are described in EP 2305238.

In one embodiment the pharmaceutical composition comprising N-acetyl-L-cysteine for the above mentioned use, where the composition is for administration at a dose of N-acetyl-L-cysteine that is between 30 and 60 mg/kg/day on days when administered. In another embodiment the pharmaceutical composition is for administration at a dose of N-acetyl-L-cysteine that is between 30 and 45 mg/kg/day on days when administered.

In one embodiment the invention provides a pharmaceutical composition comprising N-acetyl-L-cysteine for the use described above where the pharmaceutical composition is protected from light. In another embodiment the pharmaceutical composition is a water soluble tablet. In still another embodiment the pharmaceutical composition contains sodium hydrogen carbonate. In one embodiment the pharmaceutical composition is a slow-release formulation and/or a formulation for gastric protection.

In one aspect the invention provides a method for the treatment of a mammal in connection with IVF, comprising intravenously administering a pharmaceutical composition comprising N-acetyl-L-cysteine(NAC) to said mammal between 50-150 mg/kg body weight of NAC once a day for 1-3 days in connection with IVF treatment.

One aspect is a method comprising intravenous administration of NAC in a dose of 150 mg/kg for 1-3 days.

Another aspect is a method comprising intravenous administration of NAC only on the same day as IVF treatment.

The invention claimed is:

1. A method for treating an indication associated with in vitro fertilization (IVF) in a mammal comprising:
   administering N-acetyl-L-cysteine (NAC) to the mammal, wherein the NAC is administered intravenously at a dose of 50-150 mg/kg body weight for 1-3 days.

2. The method of claim 1, wherein the NAC is administered once a day.

3. The method of claim 2, wherein the NAC is administered at a dose of 50 mg/kg body weight on the same day as IVF treatment.

4. The method of claim 3, wherein the NAC is administered one hour before the IVF treatment.

5. A method for treating an indication associated with in vitro fertilization (IVF) in a mammal comprising:
   administering N-acetyl-L-cysteine (NAC) to the mammal, wherein the NAC is administered at a dose of 50 mg/kg body weight for one day or the NAC is administered orally at a dose of 30-45 mg/kg body weight for 1-3 days.

6. The method of claim 5, wherein the NAC is administered the morning of the day of IVF treatment.

7. The method of claim 5, wherein the NAC is administered once a day.

8. A method for treating an indication associated with in vitro fertilization (IVF) in a mammal comprising:
   administering N-acetyl-L-cysteine (NAC) to the mammal, wherein the NAC is orally administered at a dose of 600 mg three times a day on three consecutive days a week followed by four days without medication for three or more months prior to IVF treatment.

9. The method of claim 1, further comprising administering one or more of (i) selenium in the form of selenomethionine and (ii) melatonin or a pharmaceutically acceptable salt thereof.

10. The method of claim 9, wherein the selenium in the form of selenomethionine, when administered, is administered at a dose of 0.4-1.2 µg/kg/day; and the melatonin, when administered, is administered at a dose of 0.02-0.08 mg/kg/day.

11. The method of claim 1, wherein the NAC is administered at a dose of 150 mg/kg body weight for 1-3 days.

12. The method of claim 5, further comprising administering one or more of (i) selenium in the form of selenomethionine and (ii) melatonin or a pharmaceutically acceptable salt thereof.

13. The method of claim 12, wherein the selenium in the form of selenomethionine, when administered, is administered at a dose of 0.4-1.2 µg/kg/day; and the melatonin, when administered, is administered at a dose of 0.02-0.08 mg/kg/day.

14. The method of claim 8, further comprising administering one or more of (i) selenium in the form of selenomethionine and (ii) melatonin or a pharmaceutically acceptable salt thereof.

15. The method of claim 14, wherein the selenium in the form of selenomethionine, when administered, is administered at a dose of 0.4-1.2 µg/kg/day; and the melatonin, when administered, is administered at a dose of 0.02-0.08 mg/kg/day.

* * * * *